United States Patent
Katsoulis et al.

(10) Patent No.: US 9,920,079 B2
(45) Date of Patent: Mar. 20, 2018

(54) PROCESS FOR PRODUCTION OF HALOSILANES FROM SILICON-CONTAINING TERNARY INTERMETALLIC COMPOUNDS

(71) Applicant: Dow Corning Corporation, Midland, MI (US)

(72) Inventors: Dimitris Katsoulis, Midland, MI (US); John Roberts, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/503,462

(22) PCT Filed: Nov. 6, 2015

(86) PCT No.: PCT/US2015/059368
§ 371 (c)(1),
(2) Date: Feb. 13, 2017

(87) PCT Pub. No.: WO2016/099689
PCT Pub. Date: Jun. 23, 2016

(65) Prior Publication Data
US 2017/0275308 A1  Sep. 28, 2017

Related U.S. Application Data

(60) Provisional application No. 62/093,487, filed on Dec. 18, 2014.

(51) Int. Cl.
C07F 7/00 (2006.01)
C07F 7/16 (2006.01)
C01B 33/107 (2006.01)

(52) U.S. Cl.
CPC ............ C07F 7/16 (2013.01); C01B 33/1071 (2013.01)

(58) Field of Classification Search
CPC .............................. C07F 7/16; C01B 33/1071
USPC ........................................................ 556/473
See application file for complete search history.

(56) References Cited

U.S. PATENT DOCUMENTS

| | | | |
|---|---|---|---|
| 2,532,430 A | 12/1950 | Strether et al. | |
| 4,864,044 A | 9/1989 | Lewis et al. | |
| 5,714,131 A | 2/1998 | Margaria et al. | |
| 6,339,167 B2* | 1/2002 | Aramata ............... | C07F 7/16 556/472 |
| 8,697,900 B2 | 4/2014 | Anderson et al. | |
| 8,865,927 B2 | 10/2014 | Katsoulis et al. | |
| 2011/0158884 A1 | 8/2011 | Bentley et al. | |
| 2015/0005156 A1 | 1/2015 | Dash et al. | |
| 2015/0011789 A1 | 1/2015 | Dash et al. | |

FOREIGN PATENT DOCUMENTS

| | | |
|---|---|---|
| WO | 2013-158233 A1 | 10/2013 |
| WO | 2013-158234 A1 | 10/2013 |
| WO | 2014-099125 A1 | 6/2014 |
| WO | 2014-113124 A1 | 7/2014 |
| WO | 2014-149215 A1 | 9/2014 |
| WO | 2014-149224 A1 | 9/2015 |

OTHER PUBLICATIONS

Ding, et. al., "CuCl-Catalyzed Hydrogenation of Silicon Tetrachloride in the Presence of Silicon: Mechanism and Kinetic Modeling", Industrial & Engineering Chemistry Research, Oct. 2, 2014, pp. A-K, Shanghai, China.

* cited by examiner

*Primary Examiner* — Sudhakar Katakam
*Assistant Examiner* — Kofi Adzamli
(74) *Attorney, Agent, or Firm* — Catherine U. Brown

(57) ABSTRACT

A process for preparing a reaction product including a halosilane includes: contacting an unsaturated hydrocarbyl halide and a ternary intermetallic compound at a temperature of 300° C. to 700° C. to form the reaction product. The ternary intermetallic compound includes copper, silicon and a transition metal. The halosilane in the reaction product has formula $R1_m R^2_n\text{—}H_o SiX_{(4-m-n-o)}$, where each $R^1$ is independently a saturated monovalent hydrocarbyl group, each $R^2$ is independently an unsaturated monovalent hydrocarbyl group; each X is independently a halogen atom; subscript m is 1, 2, or 3; subscript n is 0, 1, or 2; subscript o is 0, 1, or 2; and a quantity (m+n+o) is 1, 2, or 3. At least a portion of the unsaturated hydrocarbyl groups in the unsaturated hydrocarbyl halide are converted to saturated hydrocarbyl groups ($R^1$) in the halosilane.

17 Claims, No Drawings

PROCESS FOR PRODUCTION OF HALOSILANES FROM SILICON-CONTAINING TERNARY INTERMETALLIC COMPOUNDS

This application is a U.S. national stage filing under 35 U.S.C. § 371 of PCT Application No. PCT/US15/059368 filed on 6 Nov. 2015, currently pending, which claims the benefit of U.S. Provisional Patent Application No. 62/093487 filed 18 Dec. 2014 under 35 U.S.C. § 119 (e). PCT Application No. PCT/US15/059368 and U.S. Provisional Patent Application No. 62/093487 are hereby incorporated by reference.

Methods of preparing halosilanes are known in the art. Typically, halosilanes are produced commercially by the Mueller-Rochow Direct Process, which comprises passing a halide compound over zero-valent silicon ($Si^0$) in the presence of a copper catalyst and various optional promoters. Mixtures of halosilanes are produced by the Direct Process. When an unsaturated hydrocarbyl halide is used, a mixture of organohalosilanes is produced by the Direct Process. When a hydrogen halide is used, a mixture of hydridohalosilanes is produced by the Direct Process.

The typical process for making the $Si^0$ used in the Direct Process consists of the carbothermic reduction of $SiO_2$ in an electric arc furnace. Extremely high temperatures are required to reduce the $SiO_2$, so the process is energy intensive. Consequently, production of $Si^0$ adds costs to the Direct Process for producing halosilanes. Therefore, there is a need for a more economical method of producing halosilanes that avoids or reduces the need of using $Si^0$.

Various halosilanes find use in different industries. Diorganodihalosilanes, such as dimethyldichlorosilane, are hydrolyzed to produce a wide range of polyorganosiloxanes, such as polydiorganosiloxanes. Organohydridohalosilanes can be used to make polyorganohydridosiloxanes, which are useful as waterproofing agents; alternatively organohydridohalosilanes can be used as raw materials for making other organohalosilanes. Therefore, there is a need for a method of selectively producing desired halosilanes.

BRIEF SUMMARY OF THE INVENTION

A process for preparing a reaction product comprising a halosilane comprises: contacting an unsaturated hydrocarbyl halide and a ternary intermetallic compound comprising copper (Cu), silicon (Si) and a transition metal selected from the group consisting of silver (Ag), cobalt (Co), chromium (Cr), iron (Fe), molybdenum (Mo), and rhodium (Rh) at a temperature of 300° C. to 700° C. to form the reaction product, where the halosilane has general formula $R^1_m R^2_n H_o SiX_{(4-m-n-o)}$, where each $R^1$ is independently a saturated monovalent hydrocarbyl group, each $R^2$ is independently an unsaturated monovalent hydrocarbyl group; each X is independently a halogen atom; subscript m is 1, 2, or 3; subscript n is 0, 1, or 2; subscript o is 0, 1, or 2; and a quantity (m+n+o) is 1, 2, or 3.

DETAILED DESCRIPTION OF THE INVENTION

The Brief Summary of the Invention and the Abstract are hereby incorporated by reference. All ratios, percentages, and other amounts are by weight, unless otherwise indicated. The articles "a", "an", and "the" each refer to one or more, unless otherwise indicated by the context of the specification. The prefix "poly" means more than one. Abbreviations used herein are defined in Table 1, below.

TABLE 1

| Abbreviations | |
|---|---|
| Abbreviation | Word |
| % | Percent |
| ° C. | degrees Celsius |
| Bu | "Bu" means butyl and includes various structures including nBu, sec-butyl, tBu, and iBu. |
| iBu | Isobutyl |
| nBu | normal butyl |
| tBu | tertiary butyl |
| cm | Centimeter |
| Et | Ethyl |
| FID | flame ionization detector |
| g | Gram |
| GC | gas chromatograph and/or gas chromatography |
| GC-MS | gas chromatograph- mass spectrometer and/or gas chromatography-mass spectrometry |
| hr | Hour |
| kPag | kilopascals gauge |
| Me | Methyl |
| mg | Milligram |
| min | Minutes |
| mL | Milliliters |
| Ph | Phenyl |
| Pr | "Pr" means propyl and includes various structures such as iPr and nPr. |
| iPr | Isopropyl |
| nPr | normal propyl |
| s | Seconds |
| sccm | standard cubic centimeters per minute |
| TCD | thermal conductivity detector |
| uL | Microliter |
| Vi | Vinyl |

"Alkyl" means an acyclic, branched or unbranched, saturated monovalent hydrocarbon group. Examples of alkyl groups include Me, Et, Pr, 1-methylethyl, Bu, 1-methylpropyl, 2-methylpropyl, 1,1-dimethylethyl, 1-methylbutyl, 1-ethylpropyl, pentyl, 2-methylbutyl, 3-methylbutyl, 1,2-dimethylpropyl, 2,2-dimethylpropyl, hexyl, heptyl, 2-ethylhexyl, octyl, nonyl, and decyl. Alkyl groups have at least one carbon atom. Alternatively, alkyl groups may have 1 to 12 carbon atoms, alternatively 1 to 10 carbon atoms, alternatively 1 to 6 carbon atoms, alternatively 1 to 4 carbon atoms, alternatively 1 to 2 carbon atoms, and alternatively 1 carbon atom.

"Aralkyl" and "alkaryl" each refer to an alkyl group having a pendant and/or terminal aryl group or an aryl group having a pendant alkyl group. Exemplary aralkyl groups include benzyl, tolyl, xylyl, phenylethyl, phenyl propyl, and phenyl butyl. Aralkyl groups have at least 4 carbon atoms. Monocyclic aralkyl groups may have 4 to 12 carbon atoms, alternatively 4 to 9 carbon atoms, and alternatively 4 to 7 carbon atoms. Polycyclic aralkyl groups may have 7 to 17 carbon atoms, alternatively 7 to 14 carbon atoms, and alternatively 9 to 10 carbon atoms.

"Alkenyl" means an acyclic, branched, or unbranched unsaturated monovalent hydrocarbon group, where the monovalent hydrocarbon group has a double bond. Alkenyl groups include Vi, allyl, propenyl, and hexenyl. Alkenyl groups have at least 2 carbon atoms. Alternatively, alkenyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Alkynyl" means an acyclic, branched, or unbranched unsaturated monovalent hydrocarbon group, where the monovalent hydrocarbon group has a triple bond. Alkynyl groups include ethynyl and propynyl. Alkynyl groups have at least 2 carbon atoms. Alternatively, alkynyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Aryl" means a cyclic, fully unsaturated, hydrocarbon group. Aryl is exemplified by, but not limited to, Ph and naphthyl. Aryl groups have at least 5 carbon atoms. Monocyclic aryl groups may have 6 to 9 carbon atoms, alternatively 6 to 7 carbon atoms, and alternatively 6 carbon atoms. Polycyclic aryl groups may have 10 to 17 carbon atoms, alternatively 10 to 14 carbon atoms, and alternatively 12 to 14 carbon atoms.

"Carbocycle" and "carbocyclic" refer to a hydrocarbon ring. Carbocycles may be monocyclic or alternatively may be fused, bridged, or spiro polycyclic rings. Carbocycles have at least 3 carbon atoms. Monocyclic carbocycles may have 3 to 9 carbon atoms, alternatively 4 to 7 carbon atoms, and alternatively 5 to 6 carbon atoms. Polycyclic carbocycles may have 7 to 17 carbon atoms, alternatively 7 to 14 carbon atoms, and alternatively 9 to 10 carbon atoms. Carbocycles may be saturated or partially unsaturated.

"Cycloalkyl" refers to a saturated hydrocarbon group including a saturated carbocycle. Cycloalkyl groups are exemplified by cyclobutyl, cyclopentyl, cyclohexyl, and methylcyclohexyl. Cycloalkyl groups have at least 3 carbon atoms. Monocyclic cycloalkyl groups may have 3 to 9 carbon atoms, alternatively 4 to 7 carbon atoms, and alternatively 5 to 6 carbon atoms. Polycyclic cycloalkyl groups may have 7 to 17 carbon atoms, alternatively 7 to 14 carbon atoms, and alternatively 9 to 10 carbon atoms.

"Metallic" means that the metal has an oxidation number of zero.

"Purging" means to introduce a gas stream to the reactor containing the ternary intermetallic compound to remove unwanted gaseous or liquid materials.

"Residence time" means the time which a material takes to pass through a reactor system in a continuous process, or the time a material spends in the reactor in a batch process. For example, residence time may refer to the time during which one reactor volume of the ternary intermetallic compound makes contact with the unsaturated hydrocarbyl halide as the ternary intermetallic compound passes through the reactor system in a continuous process or during which the ternary intermetallic compound is placed within the reactor in a batch process. Alternatively, residence time may refer to the time for one reactor volume of reactant gases to pass through a reactor charged with the ternary intermetallic compound, e.g., the time for one reactor volume of the unsaturated hydrocarbyl halide to pass through a reactor charged with the ternary intermetallic compound.

"Treating" means to introduce a gas stream to the reactor containing the ternary intermetallic compound to pre-treat the ternary intermetallic compound before contacting it with the unsaturated hydrocarbyl halide.

A process for preparing a reaction product comprising a halosilane comprises: contacting an unsaturated hydrocarbyl halide and a ternary intermetallic compound at a temperature of 300° C. to 700° C. to form the reaction product. The unsaturated hydrocarbyl halide may have formula $R^2X$, where each $R^2$ is independently an unsaturated monovalent hydrocarbyl group, and each X is independently a halogen atom. The ternary intermetallic compound comprises copper (Cu), silicon (Si) and a transition metal selected from the group consisting of silver (Ag), cobalt (Co), chromium (Cr), iron (Fe), molybdenum (Mo) and rhodium (Rh). The reaction product comprises a halosilane of general formula $R^1_m R^2_n H_o SiX_{(4-m-n-o)}$, where each $R^1$ is independently a saturated monovalent hydrocarbyl group, each $R^2$ is independently an unsaturated monovalent hydrocarbyl group; each X is independently a halogen atom; subscript m is 1, 2, or 3; subscript n is 0, 1, or 2; subscript o is 0, 1, or 2; and a quantity (m+n+o) is 1, 2, or 3.

In the unsaturated hydrocarbyl halide of formula $R^2X$, $R^2$ may be selected from the group consisting of alkenyl and alkynyl, as defined above. Alternatively, $R^2$ may be an alkenyl group. The alkenyl groups for $R^2$ may have 2 to 10 carbon atoms, alternatively 2 to 6 carbon atoms, alternatively 2 to 4 carbon atoms, and alternatively 2 carbon atoms. Alkenyl groups containing at least three carbon atoms may have a branched or unbranched structure. Alternatively, $R^2$ may be vinyl or allyl. Alternatively, R may be vinyl. Each halogen atom for X may be independently selected from Br, Cl or I; alternatively Br or Cl; and alternatively Cl. Examples of the unsaturated hydrocarbyl halide include, but are not limited to, vinyl chloride, vinyl bromide, vinyl iodide, allyl chloride, allyl bromide, and allyl iodide.

The ternary intermetallic compound comprises Cu, Si and a transition metal selected from Ag, Co, Cr, Fe, Mo and Rh. The ternary intermetallic compound may have an empirical formula $Co_a Cu_b Si_c Ag_d Cr_e Fe_f Mo_g Rh_h$ where subscripts b, c, d, e, f, g, and h represent the molar amounts of each element present, and a≥0, b>0, c>0, d≥0, e≥0, f≥0, g≥0 and h≥0; with the provisos that at least one of a, d, e, f, g and h is not 0. In the ternary intermetallic compound, b>c. Alternatively, 2.5≤b≤8, c=1, and one of a, d, e, f, and g is greater than 0. Alternatively, the transition metal may be selected from the group consisting of Ag, Cr, Fe, and Mo. Alternatively, the transition metal may be selected from Cr and Fe. Alternatively, the transition metal may be selected from Cr, Fe, and Rh. Alternatively, the transition metal may be Cr. Alternatively, the ternary intermetallic compound may have formula $(M)_i(Cu_kSi)_j$, where M is the transition metal selected from Ag, Co, Cr, Fe, Mo and Rh. Subscript i represents the molar amount of transition metal, and 0<i≤1. Subscript k represents the molar amount of copper relative to silicon, and 2.5≤b≤8. Alternatively, 3≤k≤5. Subscript j represents the molar amount of copper and silicon collectively, relative to the amount of the transition metal, and j has a value sufficient that a quantity (i+j)=100. Exemplary ternary intermetallic compounds include ternary intermetallic compounds of Cu, Si, and Ag; of Cu, Si, and Co; of Cu, Si, and Cr; of Cu, Si, and Fe; of Cu, Si, and Mo; and of Cu, Si, and Rh. Alternatively, the ternary intermetallic compound may have formula $(M_m:Cu_{(1-m)})_n Si$, where M is as described above. Subscript 0<m≤0.01; alternatively 0.001≤m≤0.01 and 2.5≤n≤8. Alternatively, M is selected from the group consisting of Ag, Cr, Fe, and Mo. Alternatively, M is selected from the group consisting of Ag, Cr, and Mo. Alternatively, M is Cr. Exemplary ternary intermetallic compounds include $(Ag_{0.01}Cu_{0.99})_5Si$, $(Cr_{0.01}Cu_{0.99})_5Si$, $(Fe_{0.01}Cu_{0.99})_5Si$, $(Mo_{0.01}Cu_{0.99})_5Si$, $(Rh_{0.01}Cu_{0.99})_5Si$, $(Co_{0.01}Cu_{0.99})_5Si$, $(Ag_{0.01}Cu_{0.99})_4Si$, $(Co_{0.01}Cu_{0.99})_4Si$, $(Rh_{0.01}Cu_{0.99})_4Si$, $(Cr_{0.01}Cu_{0.99})_4Si$, $(Fe_{0.01}Cu_{0.99})_4Si$, $(Mo_{0.01}Cu_{0.99})_5Si$, $(Ag_{0.01}Cu_{0.99})_3Si$, $(Cr_{0.01}Cu_{0.99})_3Si$, $(Fe_{0.01}Cu_{0.99})_3Si$, $(Mo_{0.01}Cu_{0.99})_3Si$, $(Co_{0.01}Cu_{0.99})_3Si$, and $(Rh_{0.01}Cu_{0.99})_3Si$. Ternary intermetallic compounds are commercially available. Alternatively, the ternary intermetallic compounds may be prepared by conventional methods, such as from the melt of the individual elements at predetermined stoichiometry using a heating apparatus such as electric arc melter. Alternatively, the ternary intermetallic compounds may be prepared by a process comprising vacuum impregnating two metal halides on silicon particles thereby producing a mixture, and mechanochemically processing the mixture under an inert atmosphere, thereby producing a reaction product comprising the ternary intermetallic compound. Ternary intermetallic compounds described above may be prepared in this manner.

In the process described above, an additional reactant may be added during contacting the unsaturated hydrocarbyl halide and the ternary intermetallic compound. The additional reactant may be hydrogen ($H_2$), a saturated hydrocarbyl halide, or both. The saturated hydrocarbyl halide may have formula $R^1X$, where $R^1$ and X are as described above. Alternatively, $R^1$ may be an alkyl group of 1 to 10 carbon atoms, alternatively 1 to 6 carbon atoms and alternatively 1 to 4 carbon atoms. $R^1$ may be Me, Et, Pr, or Bu; alternatively $R^1$ may be Me or Et. Examples of saturated hydrocarbyl halides include methyl chloride and ethyl chloride.

The process can be performed in any reactor suitable for the combining of gases and solids or any reactor suitable for the combining of liquids and solids. For example, the reactor configuration can be a batch vessel, packed bed, stirred bed, vibrating bed, moving bed, re-circulating beds, or a fluidized bed. Alternatively, the reactor for may be a packed bed, a stirred bed, or a fluidized bed. To facilitate reaction, the reactor should have means to control the temperature of the reaction zone.

The temperature at which the ternary intermetallic compound and the unsaturated hydrocarbyl halide are contacted is at least 300° C., alternatively 300° C. to 700° C.; alternatively 300° C. to 600° C.; alternatively 300° C. to 500° C.; alternatively 500° C. to 700° C.; alternatively 600° C. to 700° C.; alternatively 500° C. to 600° C.; alternatively 300° C. to 320° C.; alternatively 350° C. to 400° C.; alternatively 370° C. to 400° C.; and alternatively 300° C. to 400° C. Without wishing to be bound by theory, it is thought that if temperature is less than 300° C., then the reaction may not proceed at a sufficient speed to produce the desired product; and if the temperature is greater than 700° C., then the unsaturated hydrocarbyl halide and/or the halosilane in the reaction product may decompose.

The pressure at which the unsaturated hydrocarbyl halide (and, when present, the $H_2$) are contacted with the ternary intermetallic compound can be sub-atmospheric, atmospheric, or super-atmospheric. For example, the pressure may range from 0 kilopascals gauge (kPag) to 2000 kPag; alternatively 100 kPag to 1000 kPag; and alternatively 100 kPag to 800 kPag.

When hydrogen ($H_2$) is added, the mole ratio of $H_2$ to unsaturated hydrocarbyl halide contacted with the ternary intermetallic compound may range from 10,000:1 to 0.01:1, alternatively 100:1 to 1:1, alternatively 20:1 to 5:1, alternatively 20:1 to 4:1, alternatively 20:1 to 2:1, alternatively 20:1 to 1:1, and alternatively 4:1 to 1:1.

The residence time for the unsaturated hydrocarbyl halide (and, when present $H_2$) is sufficient for the unsaturated hydrocarbyl halide (and, when present $H_2$) to contact the ternary intermetallic compound and form the reaction product. For example, a sufficient residence time may be at least 0.01 s, alternatively at least 0.1 s, alternatively 0.1 s to 10 min, alternatively 0.1 s to 1 min, and alternatively 0.5 s to 10 s. The desired residence time may be achieved by adjusting the flow rate of the unsaturated hydrocarbyl halide (and when present the $H_2$), or by adjusting the total reactor volume, or by any combination thereof.

When $H_2$ is used, the unsaturated hydrocarbyl halide and $H_2$ may be fed to the reactor simultaneously; however, other methods of combining, such as by separate pulses or separate streams, are also envisioned.

The ternary intermetallic compound is present in a sufficient amount. A sufficient amount of ternary intermetallic compound is enough ternary intermetallic compound to form the halosilane when the unsaturated hydrocarbyl halide (and, when present $H_2$) is contacted with the ternary intermetallic compound. For example, a sufficient amount of ternary intermetallic compound may be at least 0.01 mg ternary intermetallic compound/cm$^3$ of reactor volume; alternatively at least 0.5 mg ternary intermetallic compound/cm$^3$ of reactor volume, and alternatively 1 mg to 10,000 mg ternary intermetallic compound/cm$^3$ of reactor volume.

There is no upper limit on the time for which the process is conducted. For example, the process may be conducted for at least 0.1 s, alternatively 1 s to 30 hr, alternatively 1 min to 8 hr, alternatively 1 hr to 5 hr, and alternatively 3 hr to 30 hr.

If the unsaturated hydrocarbyl halide is a liquid at or below standard temperature and pressure (or the temperature and pressure selected for the process), the process may further comprise vaporizing the unsaturated hydrocarbyl halide by known methods, such as pre-heating, before contacting the unsaturated hydrocarbyl halide with the ternary intermetallic compound. Alternatively, the process may further comprise bubbling the hydrogen through liquid unsaturated hydrocarbyl halide to vaporize the unsaturated hydrocarbyl halide before contacting hydrogen and unsaturated hydrocarbyl halide with the ternary intermetallic compound.

If the unsaturated hydrocarbyl halide is a solid at or below standard temperature and pressure, the process may further comprise pre-heating above the melting point and liquefying or vaporizing the unsaturated hydrocarbyl halide before contacting with the ternary intermetallic compound.

The process described herein may further comprise purging and/or treating before contacting the unsaturated hydrocarbyl halide with the ternary intermetallic compound. "Purging" and "Treating" are as defined above. This step comprises introducing an inert gas stream into the reactor containing ternary intermetallic compound. Purging and/or treating may be performed at ambient or elevated temperature, e.g., at least 25° C., alternatively at least 300° C., alternatively 25° C. to 500° C., alternatively 300° C. to 500° C. Purging may be performed to remove unwanted materials, such as $H_2$, $O_2$, $H_2O$ and/or HX, where X is as defined above. Purging and/or treating may be accomplished with an inert gas, such as $N_2$ or Ar, or with a reactive gas, such as $H_2$ or the unsaturated hydrocarbyl halide.

Alternatively, the process may optionally further comprise: contacting the ternary intermetallic compound with $H_2$ before and/or during contacting with the unsaturated hydrocarbyl halide. $H_2$ can be added to the unsaturated hydrocarbyl halide stream. Alternatively, $H_2$ and unsaturated hydrocarbyl halide can be added concurrently to the reactor in separate streams.

The process may further comprise recovering the halosilane from the reaction product. The halosilane may be recovered from the reaction product by, for example, removing gaseous product from the reactor followed by isolation by distillation. The reaction product produced by the method described and exemplified herein may comprise a halosilane of general formula $R^1{}_m R^2{}_n H_o SiX_{(4-m-n-o)}$, where each $R^1$ is independently a saturated monovalent hydrocarbyl group, each $R^2$ is independently an unsaturated monovalent hydrocarbyl group; each X is independently a halogen atom; subscript m is 1, 2, or 3; subscript n is 0, 1, or 2; subscript o is 0, 1, or 2; and a quantity (m+n+o) is 1, 2, or 3.

The process described herein selectively produces halosilanes. Using the description herein, process conditions (e.g., the selection of transition metal in the ternary intermetallic compound, relative amounts of each metal in the ternary intermetallic compound, process temperature, and the unsaturated hydrocarbyl halide selected, and whether $H_2$ is added during contacting the ternary intermetallic compound and the unsaturated hydrocarbyl halide) may be selected to produce a desired halosilane species. For example, when the transition metal is Ag, each X is a chlorine atom, $R^1$ is ethyl, and $R^2$ is vinyl, then the reaction product may comprise a mixture of halosilanes of formulae $Vi_3SiCl$, $ViSiCl_2$, $ViEtSiCl_2$, $ViSiCl_3$, $EtSiCl_3$, and $ViHSiCl_2$.

Alternatively, when the transition metal is Cr, each X is a chlorine atom, $R^1$ is ethyl, and $R^2$ is vinyl, then the reaction product may comprise a mixture of halosilanes of formulae $ViEtSiCl_2$, $EtSiCl_3$, $Et_2SiCl_2$, and $ViSiCl_3$. Alternatively, the reaction product may comprise halosilanes of formulae $Vi_3SiCl$, $Vi_2SiCl_2$, $ViEtSiCl_2$, $ViHSiCl_2$, $Et_2SiCl_2$, $ViSiCl_3$, and $EtSiCl_3$ when hydrogen is not added during contacting. Alternatively, when the transition metal is Cr, each X is a chlorine atom, $R^1$ is ethyl, and $R^2$ is vinyl and hydrogen is added during contacting, then the reaction product may comprise a mixture of halosilanes of formulae $ViEtSiCl_2$, $Et_2SiCl_2$, $ViSiCl_3$, $EtSiCl_3$, and $EtHSiCl_3$.

Alternatively, when the transition metal is Fe, each X is a chlorine atom, $R^1$ is ethyl, and $R^2$ is vinyl, then the reaction product may comprise a mixture of halosilanes of formulae $Vi_2SiCl_2$, $ViEtSiCl_2$, $Et_2SiCl_2$, $ViSiCl_3$, $EtSiCl_3$, and $ViHSiCl_2$.

Alternatively, when the transition metal is Mo, each X is a chlorine atom, $R^1$ is ethyl, and $R^2$ is vinyl, then the reaction product may comprise a mixture of halosilanes of formulae $Vi_2SiCl_2$, $ViEtSiCl_2$, $Et_2SiCl_2$, $ViSiCl_3$, $ViSiCl3$, $ViHSiCl_2$, and $EtHSiCl_2$.

The process described herein provides an unexpected benefit in that at least a portion of the unsaturated hydrocarbyl groups ($R^2$) in the unsaturated hydrocarbyl halide are converted to saturated hydrocarbyl groups ($R^1$) in the halosilane, and this beneficial technical effect is observed even when the additional reactant, i.e., hydrogen and/or unsaturated hydrocarbyl halide, is not added during contacting the unsaturated hydrocarbyl halide and the ternary intermetallic compound.

EXAMPLES

These examples are intended to illustrate some embodiments of the invention and should not be interpreted as limiting the scope of the invention set forth in the claims.

All reactions were run in a ¼" quartz tube reactor inside a ⅜" stainless tube used for heating. The reactor effluent was analyzed with a GC, and individual organic components and other by-products were not quantified. Vinyl chloride (VCM) conversion to silanes is reported in Table 1. Samples of ternary intermetallic compounds of the composition $(M:Cu)_5Si$, where M represents the transition metal and the mole ratio of transition metal:copper was 1:99, were prepared. Each ternary intermetallic compound was placed in the reactor and contacted with vinyl chloride at a temperature of 300° C. The vinyl chloride was fed into the reactor at a rate of 5 sccm. Pressure in the reactor was 1 psi (6.89 kPag). The ternary intermetallic compound was present in an amount sufficient to provide 0.25 g of Si in the reactor in each example. When an asterisk, '*', is shown by the metal, this indicates that 10 sccm $H_2$ co-feed was fed into the reactor with the vinyl chloride. The transition metal used and results are shown in Table 1, below.

TABLE 1

Transition Metal Used and Results

| Example | Metal | $Vi_3SiCl$ | $Vi_2SiCl_2$ | $ViEtSiCl_2$ | $Et_2SiCl_2$ | $ViSiCl_3$ | $EtSiCl_3$ | $ViHSiCl_2$ | $EtHSiCl_2$ | $HSiCl_3$ | $SiCl_4$ | VCM Conv. |
|---|---|---|---|---|---|---|---|---|---|---|---|---|
| 1 | Fe | 0 | 24 | 6 | 5 | 8 | 54 | 3 | 0 | 0 | 0 | 7.8 |
| 2 | Cr | 17 | 10 | 1 | 21 | 18 | 30 | 7 | 0 | 0 | 0 | 11.5 |
| 3 | Cr* | 0 | 0 | 13 | 1 | 6 | 6 | 0 | 79 | 0 | 0 | 15 |
| 4 comparative | Al | 0 | 0 | 0 | 0 | 0 | 0 | 0 | 0 | 0 | 0 | 0 |
| 5 comparative | Zn | 0 | 43 | 54 | 0 | 0 | 0 | 0 | 3 | 0 | 0 | 0.4 |
| 6 | Ag | 3 | 59 | 11 | 0 | 19 | 4 | 3 | 0 | 0 | 0 | 6.3 |
| 7 | Rh | 0 | 0 | 0 | 0 | 27 | 23 | 2 | 5 | 15 | 26 | 11 |
| 8 | Mo | 0 | 28 | 4 | 11 | 14 | 34 | 7 | 2 | 0 | 0 | 5.8 |
| 9 comparative | Mn | 0 | 59 | 0 | 0 | 21 | 0 | 20 | 0 | 0 | 0 | 1.2 |
| 10 | Co | 1 | 44 | 29 | 2 | 13 | 5 | 6 | 0 | 0 | 0 | 4.9 |

All values for selectivities for each halosilane in the reaction product and for VCM conversion in Table 1 are in mole %.

These examples show that even with reaction conditions that have not been optimized, significant vinyl chloride conversion (5% or greater) is observed using the process of this invention, and in each run, conversion of vinyl groups provided by the vinyl chloride to ethyl groups in the halosilane of the reaction product was observed. In the comparative example with Al as the transition metal, no reaction product formed under the conditions tested in this example. In the comparative example with Mn as the transition metal, no conversion of vinyl groups from the vinyl chloride to ethyl groups in the halosilane of the reaction product was observed. In the comparative example with Zn as the transition metal, reaction of vinyl chloride with the ternary intermetallic compound occurred at an amount of only 0.4%, therefore, insufficient reactivity for a commercial scale production process was observed for this ternary intermetallic compound under the conditions tested. These examples show that vinyl chloride reacts with certain ternary intermetallic compounds under the conditions evaluated. With certain transition metals present in the ternary intermetallic compound, the beneficial effect of converting at least a portion of the vinyl groups provided by the vinyl chloride to ethyl groups in the halosilanes of the reaction products is achieved by the process described herein.

With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. The enumerated ranges and subranges sufficiently describe and enable various embodiments of the present disclosure, and such ranges and subranges may be further delineated into relevant halves, thirds, quarters, fifths, and so on. As just one example, a range of "300 to 700" may be further delineated into a lower third, i.e., 300 to 433, a middle third, i.e., 434 to 566, and an upper third, i.e., 567 to 700, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 0.1%" inherently includes a subrange from 0.1% to 35%, a subrange from 10% to 25%, a subrange from 23% to 30%, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range of "1 to 9" includes various individual integers, such as 3, as well as individual numbers including a decimal point (or fraction), such as 4.1, which may be relied upon and provide adequate support for specific embodiments within the scope of the appended claims.

The subject matter of all combinations of independent and dependent claims, both singly and multiply dependent, is expressly contemplated but is not described in detail for the sake of brevity. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A process for preparing a reaction product comprising a halosilane, where the process comprises contacting an unsaturated hydrocarbyl halide and a ternary intermetallic compound comprising copper, silicon and a transition metal selected from the group consisting of silver, chromium, iron, molybdenum, and rhodium at a temperature from 300° C. to 700° C. to form the reaction product, where the halosilane has general formula $R^1{}_m R^2{}_n H_o SiX_{(4-m-n-o)}$, where each $R^1$ is independently a saturated monovalent hydrocarbyl group, each $R^2$ is independently an unsaturated monovalent hydrocarbyl group; each X is independently a halogen; m is 1, 2, or 3; subscript n is 0, 1, or 2; subscript o is 0, 1, or 2; and a quantity (m+n+o) is 1, 2, or 3; where at least a portion of unsaturated hydrocarbyl groups in the unsaturated hydrocarbyl halide are converted saturated hydrocarbyl groups in the halosilane.

2. The process of claim 1, further comprising one or more steps, where the one or more steps are selected from:
   purging and/or treating a reactor containing the ternary intermetallic compound before contacting the unsaturated hydrocarbyl halide and the ternary intermetallic compound; and/or
   vaporizing the unsaturated hydrocarbyl halide before contacting the unsaturated hydrocarbyl halide and the ternary intermetallic compound; and/or
   liquefying the unsaturated hydrocarbyl halide before contacting the unsaturated hydrocarbyl halide and the ternary intermetallic compound; and/or
   contacting the ternary intermetallic compound with $H_2$ before contacting the ternary intermetallic compound and the unsaturated hydrocarbyl halide; and/or
   recovering the halosilane from the reaction product.

3. The process of claim 1, further comprising adding hydrogen during contacting the unsaturated hydrocarbyl halide and the ternary intermetallic compound.

4. The process of claim 1, where the transition metal is Ag, each $R^1$ is ethyl, each $R^2$ is vinyl, and each X is chloro.

5. The process of claim 4, where the reaction product comprises halosilanes of formulae $Vi_3SiCl$, $ViSiCl_2$, $ViEtSiCl_2$, $ViSiCl_3$, $EtSiCl_3$, and $ViHSiCl_2$, where Vi represents vinyl and Et represents ethyl.

6. The process of claim 1, where the transition metal is Cr, each $R^1$ is vinyl, each $R^2$ is ethyl, and each X is chloro.

7. The process of claim 6, where the reaction product comprises halosilanes of formulae: $Vi_3SiCl$, $ViSiCl_2$, $ViEtSiCl_2$, $ViSiCl_3$, $EtSiCl_3$, and $ViHSiCl_2$, where Vi represents vinyl and Et represents ethyl.

8. The process of claim 1, where the transition metal is Fe, each $R^1$ is vinyl, each $R^2$ is ethyl, and each X is chloro.

9. The process of claim 8, where the reaction product comprises halosilanes of formulae: $Vi_2SiCl_2$, $ViEtSiCl_2$, $Et_2SiCl_2$, $ViSiCl_3$, $EtSiCl_3$, and $ViHSiCl_2$, where Vi represents vinyl and Et represents ethyl.

10. The process of claim 1, where the transition metal is Mo, each $R^1$ is vinyl, each $R^2$ is ethyl, and each X is chloro.

11. The process of claim 10, where the reaction product comprises halosilanes of formulae $Vi_2SiCl_2$, $ViEtSiCl_2$, $Et_2SiCl_2$, $ViSiCl_3$, $EtSiCl_3$, $ViHSiCl_2$, and $EtHSiCl_2$, where Vi represents vinyl and Et represents ethyl.

12. The process of claim 1, where the transition metal is Rh, each $R^1$ is vinyl, each $R^2$ is ethyl, and each X is chloro.

13. The process of claim 12, where the reaction product comprises halosilanes of formulae $ViSiCl_3$, $EtSiCl_3$, $ViHSiCl_2$, and $EtHSiCl_2$, where Vi represents vinyl and Et represents ethyl.

14. The process of claim 1, further comprising adding a saturated hydrocarbyl halide during contacting the unsaturated hydrocarbyl halide and the ternary intermetallic compound.

15. A process comprising:
(1) preparing a reaction product comprising a halosilane by a process comprising contacting an unsaturated hydrocarbyl halide and a ternary intermetallic compound comprising copper, silicon and a transition metal selected from the group consisting of silver, chromium, iron, molybdenum, and rhodium at a temperature from 300° C. to 700° C. to form the reaction product, where the halosilane has general formula $R^1{}_m R^2{}_n H_o SiX_{(4-m-n-o)}$, where each $R^1$ is independently a saturated monovalent hydrocarbyl group, each $R^2$ is independently an unsaturated monovalent hydrocarbyl group; each X is independently a halogen; m is 1, 2, or 3; subscript n is 0, 1, or 2; subscript o is 0, 1, or 2; and a quantity (m+n+o) is 1, 2, or 3; where at least a portion of unsaturated hydrocarbyl groups in the unsaturated hydrocarbyl halide are converted saturated hydrocarbyl groups in the halosilane, and (2) using the halosilane as a reactant in a process to make a product selected from polydiorganosiloxanes, polyorganohydridosiloxanes, or different organohalosilanes.

16. The process of claim 15, further comprising one or more steps before step (2), where the one or more steps are selected from:

purging and/or treating a reactor containing the ternary intermetallic compound before contacting the unsaturated hydrocarbyl halide and the ternary intermetallic compound; and/or vaporizing the unsaturated hydrocarbyl halide before contacting the unsaturated hydrocarbyl halide and the ternary intermetallic compound; and/or liquefying the unsaturated hydrocarbyl halide before contacting the unsaturated hydrocarbyl halide and the ternary intermetallic compound; and/or contacting the ternary intermetallic compound with $H_2$ before contacting the ternary intermetallic compound and the unsaturated hydrocarbyl halide; and/or recovering the halosilane from the reaction product.

17. The process of claim 15, further comprising adding hydrogen during contacting the unsaturated hydrocarbyl halide and the ternary intermetallic compound.

\* \* \* \* \*